(12) United States Patent
Murata et al.

(10) Patent No.: US 9,779,973 B2
(45) Date of Patent: Oct. 3, 2017

(54) PURGING DEVICE AND PURGING METHOD

(71) Applicant: Murata Machinery, Ltd., Kyoto, Kyoto (JP)

(72) Inventors: Masanao Murata, Ise (JP); Mitsuya Tokumoto, Inuyama (JP); Takashi Yamaji, Ise (JP); Naruto Adachi, Inuyama (JP)

(73) Assignee: MURATA MACHINERY, LTD., Kyoto (JP)

( * ) Notice: Subject to any disclaimer, the term of this patent is extended or adjusted under 35 U.S.C. 154(b) by 23 days.

(21) Appl. No.: 15/022,427

(22) PCT Filed: Jul. 17, 2014

(86) PCT No.: PCT/JP2014/069018
§ 371 (c)(1),
(2) Date: Mar. 16, 2016

(87) PCT Pub. No.: WO2015/045582
PCT Pub. Date: Apr. 2, 2015

(65) Prior Publication Data
US 2016/0225648 A1    Aug. 4, 2016

(30) Foreign Application Priority Data
Sep. 26, 2013 (JP) ................. 2013-199589

(51) Int. Cl.
*H01L 21/67* (2006.01)
*H01L 21/673* (2006.01)
(Continued)

(52) U.S. Cl.
CPC ... *H01L 21/67393* (2013.01); *G01N 33/0036* (2013.01); *G05D 7/0617* (2013.01);
(Continued)

(58) Field of Classification Search
CPC ......... H01L 21/67017; H01L 21/67769; H01L 21/67393; H01L 21/67389; G05D 7/0617; G01N 33/0036
See application file for complete search history.

(56) References Cited

U.S. PATENT DOCUMENTS 6,635,116 B1 * 10/2003 Mayeda .............. C23C 16/4401
118/715
6,729,823 B2 * 5/2004 Sakata .............. H01L 21/67017
414/217
(Continued)

FOREIGN PATENT DOCUMENTS

| | | |
|---|---|---|
| EP | 1 143 491 A1 | 10/2001 |
| JP | 2012-248785 A | 12/2012 |
| WO | 00/31780 | 2/2000 |

OTHER PUBLICATIONS

English translation of of the International Preliminary Report on Patentability dated Apr. 7, 2016 issued in counterpart International Application No. PCT/JP2014/069018.
(Continued)

*Primary Examiner* — Umashankar Venkatesan
(74) *Attorney, Agent, or Firm* — DLA Piper LLP (US)

(57) ABSTRACT

The safety of a worker is ensured, and the area in which purging is halted is limited to the minimum. The inner space of a device is divided into a working area and a non-working area, and purging of articles in the working area is halted and the purging of the articles in the non-working area is continued. The oxygen concentration in the working area is measured, and if the oxygen concentration of the working area decreases to a predetermined value or less, the purging of the articles in the non-working area is halted.

9 Claims, 5 Drawing Sheets

(51) Int. Cl.
    *H01L 21/677*     (2006.01)
    *G01N 33/00*     (2006.01)
    *G05D 7/06*     (2006.01)

(52) U.S. Cl.
    CPC .. *H01L 21/67017* (2013.01); *H01L 21/67389* (2013.01); *H01L 21/67769* (2013.01)

(56) References Cited

U.S. PATENT DOCUMENTS

| | | | | |
|---|---|---|---|---|
| 7,134,825 | B1* | 11/2006 | Schmutz | H01L 21/67769 414/217.1 |
| 8,088,203 | B2* | 1/2012 | Matsuba | B65G 1/00 454/187 |
| 9,412,634 | B2* | 8/2016 | Segawa | H01L 21/67389 |
| 2012/0309286 | A1 | 12/2012 | Nakano | 454/305 |
| 2014/0014227 | A1* | 1/2014 | Shin | H01L 21/67772 141/59 |
| 2014/0305540 | A1* | 10/2014 | Oyama | H01L 21/67389 141/4 |
| 2014/0366983 | A1* | 12/2014 | Takahara | F17C 13/02 141/197 |
| 2015/0000765 | A1* | 1/2015 | Otsuka | H01L 21/67769 137/356 |
| 2015/0004899 | A1* | 1/2015 | Otsuka | F24F 3/161 454/341 |

OTHER PUBLICATIONS

Japanese language International Search Report dated Oct. 21, 2014 and its English language translation issued in corresponding PCT application PCT/JP2014/069018.

* cited by examiner

F I G. 2
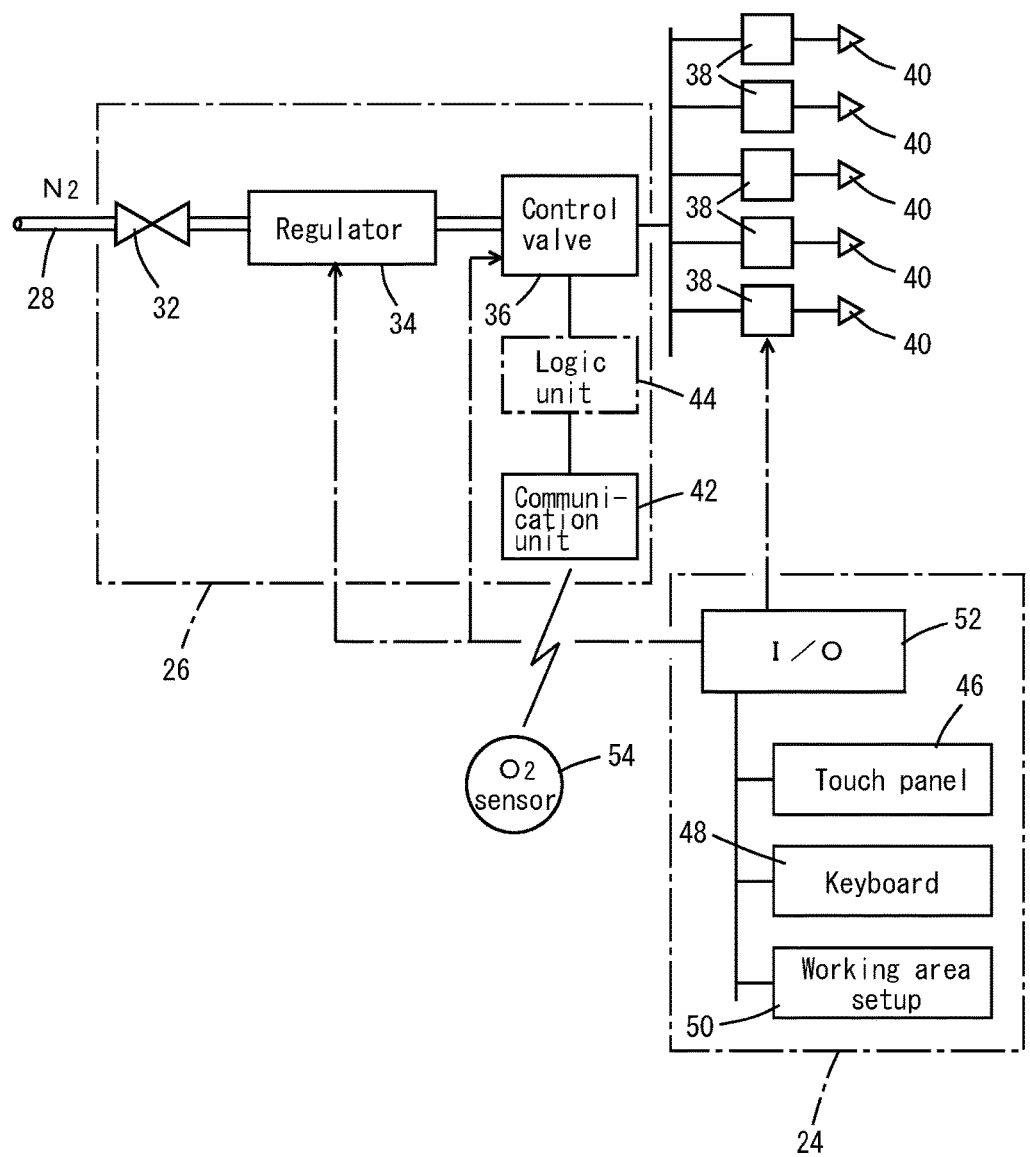

PURGING DEVICE AND PURGING METHOD

BACKGROUND OF THE INVENTION

1. Field of the Invention

The present invention relates to a purging device and a purging method for a stocker or the like, and in particular to one which monitors oxygen concentrations in the purging device.

2. Description of the Related Art

In semiconductor factories, articles such as semiconductor wafers or reticles are accommodated in a container such as a FOUP, and the container is stored in a stocker. Stockers encompass a purge stocker in which purging is performed with a purge gas such as a nitrogen gas (Patent Literature 1: JP 2012-248785). In the purge stocker, each cell of the stocker is provided with a purge gas nozzle, and by putting the nozzle in contact with a gas inlet hole of a container such as a FOUP, a purge gas is blown into the container. The blown-in purge gas is discharged from the container to the inner space or the like of the purge stocker. Clean air is blown into the purge stocker from its ceiling part, and is discharged from its underfloor and the like, and thus the oxygen concentration of the inner space of the purge stocker depends on the relationship between discharge of the purge gas from the containers and the flow of the air from the ceiling part.

A conventional technique relating to a purging device will be described. Patent Literature 2 (WO00/31780) discloses that two types of purge gases, namely, an inert gas and clean dry air are supplied; when a worker enters the purging device under consideration for maintenance or the like, the purge gas is switched to the clean dry air, and otherwise purging is regularly performed with the inert gas.

CITATION LIST

Patent Literatures

Patent Literature 1: JP 2012-248785
Patent Literature 2: WO00/31780

SUMMARY OF THE INVENTION

It is inefficient that purging is totally halted when a worker enters the purging device for maintenance or the like. However, it is also problematic to rely on an oxygen concentration sensor while the purging is continued. First, in the purging device, the flow of the purge gas and the flow of the clean air are mixed and the oxygen concentration changes significantly. Therefore, reliable detection is difficult. Second, due to the purge gas, an average of the oxygen concentrations is reduced. Accordingly, an allowable range of a decrease in the oxygen concentration is small.

It is an object of the present invention to limit an area in which purging is halted to the minimum while ensuring the safety of a worker.

The present invention relates to a purging device that performs purging with a purge gas on a plurality of articles that are supplied from outside to an inner space of the purging device, comprising:

a setup unit configured to set up a working area in which a worker works such that the inner space of the purging device is divided into the working area and a non-working area;

a purge gas control mechanism configured to control supply of the purge gas such that the purging of the articles is halted in the working area and is continued in the non-working area; and an oxygen concentration measuring device configured to measure an oxygen concentration in the working area, the purge gas control mechanism being configured to halt the purging of the articles in the non-working area if the oxygen concentration in the working area decreases to a predetermined value or less.

Furthermore, the present invention relates to a purging method for performing, using a purging device, purging with a purge gas on a plurality of articles that are supplied from outside to an inner space of the purging device, the method comprising:

a step for setting up a working area in which a worker works such that the inner space of the purging device is divided into the working area and a non-working area;

a step for causing the purging device to control supply of the purge gas such that the purging of the articles is halted in the working area and is continued in the non-working area;

a step for measuring an oxygen concentration in the working area; and a step for causing the purging device to halt the purging of the articles in the non-working area if the oxygen concentration in the working area decreases to a predetermined value or less.

According to the present invention, since the purging of the articles in the working area is halted and the purging of the articles in the non-working area is not halted, the area in which the purging is halted is small. Furthermore, in the working area, the purging of the article is halted and thus a high oxygen concentration is maintained. If the oxygen concentration in the working area decreases, the purging of the articles in the non-working area will also be halted. Accordingly, the problem that the purge gas enters the working area is solved, and the oxygen concentration increases. In this specification, descriptions regarding the purging device apply directly to the purging method. In a case of a large purge stocker, the non-working area may further be divided into an area that is adjacent to the working area, an area that is not adjacent to the working area, and the like. In this case, depending on a decrease in the oxygen concentration in the working area, the purging of the articles in the adjacent area may first be halted, and the purging of the articles in the non-adjacent area may also be halted if the oxygen concentration in the working area does still not recover.

Preferably, the oxygen concentration measuring device includes an oxygen concentration sensor configured to be carried by the worker, or an oxygen concentration sensor and a sampling tube connected to the oxygen concentration sensor, the sampling tube being configured to be carried by the worker. Since the oxygen concentration is measured at the position at which the worker is located, detection of the oxygen concentration is highly reliable. Note that the oxygen concentration sensor connected to the sampling tube may be placed in the inside or outside of the purging device. Furthermore, it is preferable that a pump for sucking an atmosphere from the sampling tube be provided.

More preferably, a partition configured to separate the working area from the non-working area and to be installed in and removed from the inner space of the purging device is further provided, and the oxygen concentration measuring device is attached to the partition so as to measure the oxygen concentration on the working area side. Preferably, the oxygen concentration measuring device is attached to the partition on the working area side. The partition is located at the boundary between the working area and the non-working area, namely, at the position at which the worker is likely to be affected by the purge gas. By measuring the oxygen concentration at this position, the oxygen concentration around the worker is detected before decreasing. Note that by configuring the partition so that it rectifies an air current, the purge gas that enters the working area from the non-working area is reduced. Furthermore, by attaching the oxygen concentration measuring device to the partition, the worker does not need to carry the oxygen concentration measuring device, making the work easy. Furthermore, if the stocker includes a transport device such as a stacker crane, the partition also serves as a limit for the entrance of the transport device.

The embodiment will describe the purge stocker, but the present invention is also applicable to an EFEM (Equipment Front End Module), a semiconductor processing device, a storage device in which bare semiconductor wafers, bare reticles, or the like are stored without being accommodated in containers, or the like. It is particularly efficient if the present invention is applied to a large purge stocker including a plurality of transport devices, since it is sufficient to halt purging only in a part of the inner space of the purge stocker.

The purging device is, for example, a purge stocker that has a door through which the worker enters and exits the inner space of the device. Furthermore, the inner space is provided with a rack in which a plurality of cells are arranged along a horizontal direction and a vertical direction, and a transport device configured to transport the articles. The cells of the rack respectively have nozzles for supplying a nitrogen gas serving as the purge gas into the articles. The inner space is configured to be supplied with clean air from a ceiling part, and the oxygen concentration of the inner space depends on a flow of the nitrogen gas discharged from the articles and a down flow of the clean air from the ceiling part. The setup unit is configured and programmed to set up the working area in terms of a column of cells along the vertical direction such that the working area continuously covers a region from the door to an area in which the worker performs a work. Accordingly, the continuous region from the door to the area in which the worker performs a work such as maintenance becomes the working area, and the oxygen concentration in the working area is increased, ensuring a safe work by measuring the oxygen concentration.

Furthermore, by the purge gas control mechanism including a communication unit configured to directly communicate with the oxygen sensor, the supply of the purge gas to the non-working area is reliably halted in case of a decrease in the oxygen concentration. Furthermore, it is preferable that a plurality of the oxygen sensors are provided, the communication unit directly communicates with the plurality of oxygen sensors, and the purge gas control mechanism includes a logic unit configured to detect a decrease in the oxygen concentration in the working area based on a combination of signals of the plurality of oxygen sensors from the communication unit. Accordingly, a decrease in the oxygen concentration is accurately detected by: an AND operation, an OR operation, or the like of the signals of the oxygen concentration sensors.

BRIEF DESCRIPTION OF THE DRAWINGS

FIG. 2 is a block diagram illustrating the purging device.

DETAILED DESCRIPTION OF THE PREFERRED EMBODIMENT

Figure 1:
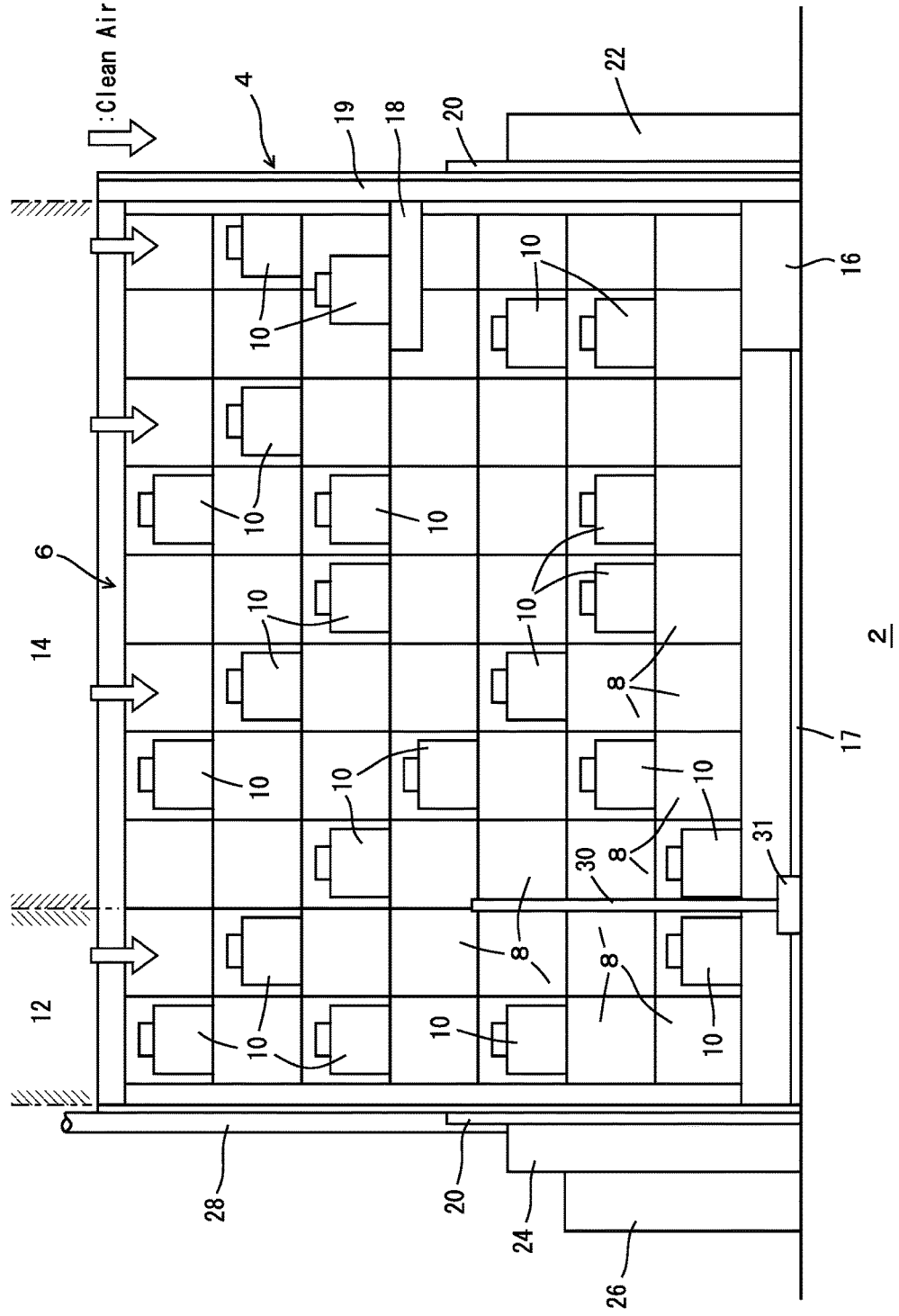
FIG. 1 is a diagram schematically illustrating a stocker including a purging device according to an embodiment.

Hereinafter, the best mode for implementing the present invention will be described. The scope of the invention should be construed according to the understanding of a person skilled in the art based on the description of the claims, in view of the description of the specification and well known techniques in this field.

Embodiment

FIGS. 1 to 7 show a purge stocker 2 and control of purging according to an embodiment. The purge stocker 2 is installed in a clean room, and a down flow of clean air is blown from a ceiling part. A fan filter unit may be provided on the ceiling part of the purge stocker 2. The housing of the purge stocker 2 and its inside are referred to as a stocker main body 4. The reference numeral 6 denotes its inner space in which articles 10 such as FOUPs are stored in cells 8 and a transport device such as a stacker crane 16 operates, and that a worker enters to perform a work such as maintenance. The plurality of cells 8 constitute a rack, and are respectively provided with pipes for a purge gas such as a nitrogen gas so that the inside of the articles 10 is purged. The oxygen concentration of the inner space 6 depends on the balance between the down flow from the ceiling part and the purge gas discharged from the articles 10, and these gases are discharged from the lower part or the like of the stocker main body 4. The plurality of cells 8 are arranged along the horizontal direction and the vertical direction, so as to constitute the rack. The article 10 such as a FOUP is a container for semiconductor wafers, has a purge gas inlet hole, and takes the purge gas from a nozzle provided for the corresponding cell.

The inner space 6 is divided into a working area 12 and a non-working area 14, and the boundary between the areas 12 and 14 extends vertically in the embodiment. In the case of a purge stocker including a plurality of layers along the height direction, the inner space 6 may be divided into the working area and the non-working area according to the layers along the height direction. Assume that the cells 8 aligned along the height direction serve as a rack column, the working area 12 is set up, in terms of, for example, columns, so as to cover a region from a door 20 through which the worker enters and exits the inner space 6 to an area in which the worker performs a work.

The stacker crane 16 is guided by a rail 17 to travel along the rack, and moves an elevating pedestal 18 up and down along a mast 19 to transport the articles 10 into and out of the cells 8. The type of the transport device that is installed in the purge stocker 2 is not limited to the stacker crane 16 but arbitrary.

The reference numeral 22 denotes a stocker controller that controls the stacker crane 16, manages inventory and entering/dispatching in the purge stocker 2, and communicates with an upstream controller (not shown) or the like. The reference numeral 24 denotes a purging controller that controls purging. The reference numeral 26 denotes a purge gas control board that has a valve for controlling a purge gas and the like, and the purging controller 24 and the purge gas control board 26 may be integrated into one piece. Furthermore, the purging controller 24 may be integrated with the stocker controller 22 into one piece. The reference numeral 28 denotes a purge gas pipe that supplies a purge gas such as a nitrogen gas to the purge gas control board 26.

The reference numeral 30 denotes a partition that is placed at the boundary between the working area 12 and the non-working area 14, is supported by a leg 31, and is configured to move. The position at which the partition 30 is placed serves also as a limit for the entrance range of the stocker crane 16.

As shown in FIG. 2, a purging device includes the purging controller 24, the purge gas control board 26, and a mass flow controller 38 and a nozzle 40 that are provided in each cell, and a pipe therebetween. The purge gas control board 26 includes a hand-operated valve 32, a regulator 34 for stabilizing pressure on the downstream side, and a control valve 36, which may be an electromagnetic valve or a pneumatic valve. A communication unit 42 receives an oxygen concentration in the working area from an oxygen concentration sensor 54, and if the oxygen concentration has a predetermined value or less, the control valve 36 is closed to stop supplying a purge gas to the entire purge stocker. The communication between the communication unit 42 and the oxygen concentration sensor 54 may be wired communication, optical communication, wireless communication, infrared communication, or the like.

If there are a plurality of oxygen concentration sensors 54, for example, if a plurality of oxygen concentration sensors are attached to the partition, an AND operation or an OR operation is performed on signals of the plurality of oxygen concentration sensors, or a logic unit 44 that subjects the signals of the oxygen concentration sensors to signal processing such as averaging or differential processing may be provided. The control valve 36 is a valve for use for the entire purge stocker and the mass flow controllers 38 stop purging in the working area, but a control valve may be provided for each column of cells, and halting of the purging in the working area and halting of the purging in the non-working area may be performed by the control valves.

The purging controller 24 includes a touch panel 46 and a keyboard 48, and upon input of a range of the working area from these input means, a working area setup unit 50 performs processing relating to setting up of the working area. In other words, the working area setup unit 50 sets up, via an input/output 52, the target flow rates of the flow controllers 38 in the working area to 0, and notifies the stocker controller of the range of the working area. On the other hand, the stocker controller restricts entrance of the stacker crane into the working area.

Figure 3:
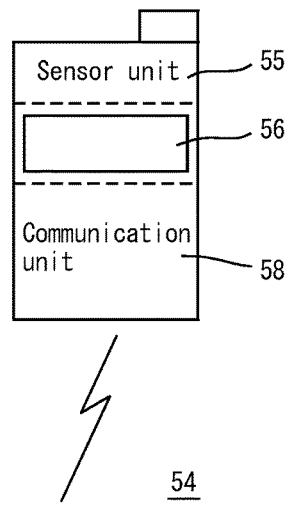
FIG. 3 is a diagram illustrating a portable oxygen concentration sensor.

FIG. 3 illustrates a portable oxygen concentration sensor 54. A sensor unit 55 accommodates a sensor of a galvanic cell type or the like and a display unit 56 displays the oxygen concentration and performs warning using a buzzer, a sound, blinking of warning light, or the like if the oxygen concentration decreases to a predetermined value or less. A communication unit 58 communicates the oxygen concentration or whether or not the oxygen concentration is within an acceptable range with the communication unit 42. Then, the worker works in the working area with the oxygen concentration sensor 54 set in her or his breast pocket or the like.

Figure 4:
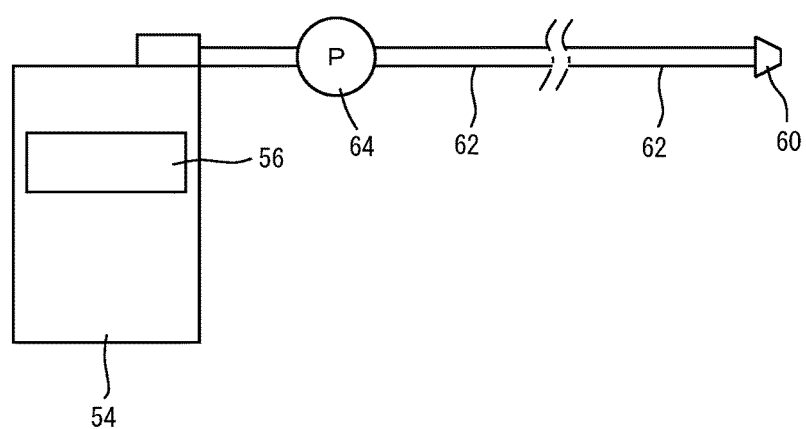
FIG. 4 is a diagram illustrating a sampling tube and the oxygen concentration sensor.

FIG. 4 illustrates a sampling tube 62 that is worn by the worker. The reference numeral 60 denotes a nozzle that sucks an atmosphere, and the sampling tube 62 is flexible and sucks a gas using an air pump 64, and the oxygen concentration sensor 54 measures the oxygen concentration, and communicates with a communication unit on the above-described control valve side. In this case, the oxygen concentration sensor does not need to be portable, and may be placed on the outside of the stocker main body, or in the inner space of the stocker main body.

Figure 5:
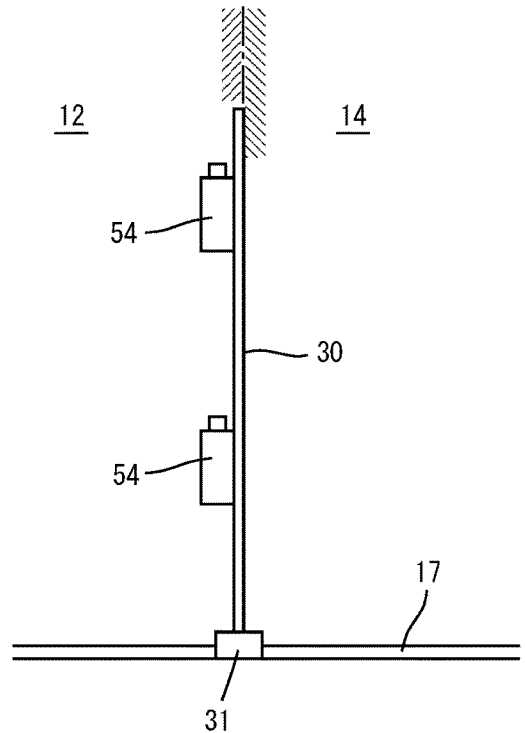
FIG. 5 is a side view illustrating a partition used in the embodiment.

FIG. 5 shows the partition 30, and the partition 30 may be non-airtight palisade-shaped or an airtight sheet. Both cases have a rectifying effect, and restrict the flow of the purge gas into the working area 12 from the non-working area 14. The partition 30 indicates a boundary of an area that the stacker crane does not enter, and is configured to be installed and moved by being carried by an worker, and one or a plurality of oxygen concentration sensors 54 are attached to the partition 30 on the working area 12 side so as to communicate with the communication unit on the control valve side.

If there are a plurality of oxygen concentration sensors 54, and the fluctuation of an air current is significant, purging in the non-working area is halted based on signals (AND signal) from the plurality of oxygen concentration sensors 54 that indicate a decrease in the oxygen concentration to a predetermined value or less. If the fluctuation in the air current is small, the purging in the non-working area is halted based on a signal (OR signal) from any one of the oxygen concentration sensors 54 that indicates a decrease in the oxygen concentration to the predetermined value or less.

Figure 6:
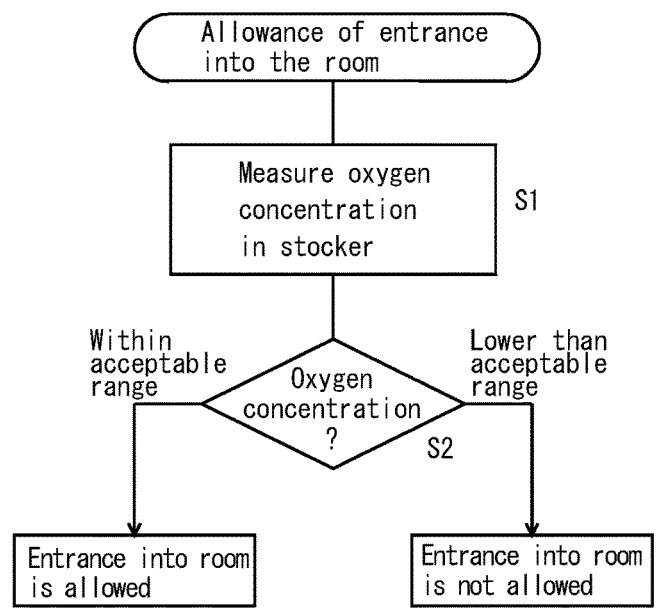
FIG. 6 is a flowchart of an algorithm for allowing entrance into the room.

FIG. 6 shows an algorithm for allowing entrance into the stocker main body (entrance into the room). The oxygen concentration in the stocker (inner space thereof) is measured by bringing the oxygen concentration sensor into the inner space of the stocker, inserting the sampling tube into the inner space of the stocker, or using an oxygen concentration sensor fixed to the inner space of the stocker (step S1). If the oxygen concentration is within an acceptable range, the entrance into the room is allowed, and if the oxygen concentration has a value lower than the acceptable range, the entrance into the room is not allowed (step S2).

Figure 7:
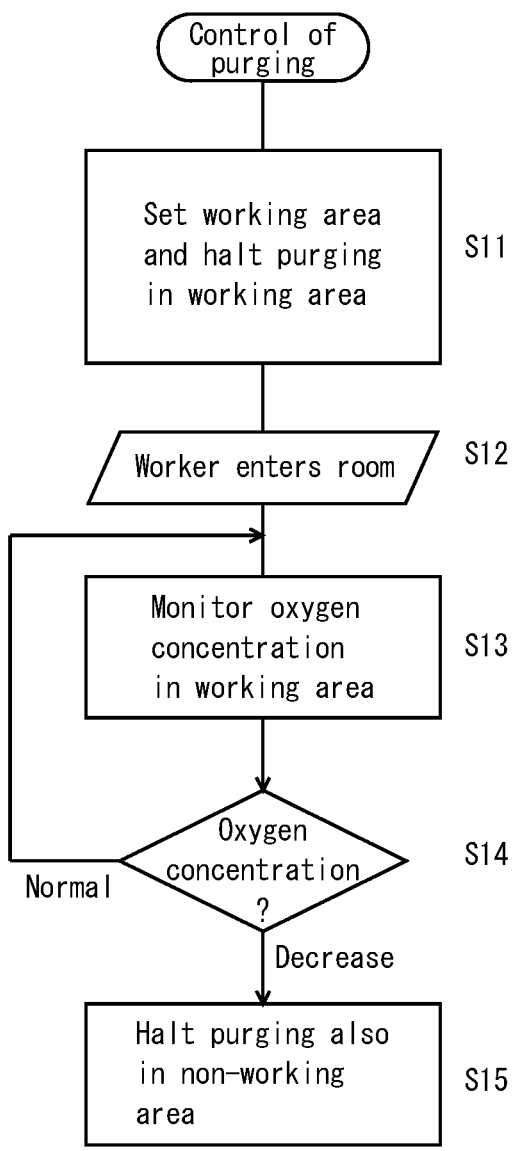
FIG. 7 is a flowchart of a purging controlling algorithm.

FIG. 7 shows a purging control algorithm when the worker enters the inner space. In step S11, the working area is set up, and purging in the working area is halted. For example, after this step, the processing of FIG. 6 is executed, and the worker enters the room (step S 12). Note that at this time, a configuration is also possible in which the purging in the non-working area is temporarily halted, and then restarted after the worker has entered the inner space. The oxygen concentration in the working area is monitored (step S13), and if the oxygen concentration decreases to a minimum acceptable value or less (step S14), the purging in the non-working area will also be halted (step S15). After being halted, the purging may be restarted when the oxygen concentration returns to a normal value, or may remain halted until the worker exits the inner space.

The embodiment has the following features:

1) Since purging is halted only in the working area, the area in which purging is halted is small;

2) Since purging is halted in the working area, the oxygen concentration is not likely to decrease. Furthermore, if the oxygen concentration in the working area decreases, the purging in the non-working area will be halted and the oxygen concentration is recovered;

3) Since the oxygen concentration sensor and the communication unit on the control valve side communicate with each other directly without using a controller or the like, the purging is reliably halted at the time of a decrease in the oxygen concentration;

4) By the worker carrying the oxygen concentration sensor or the sampling tube, the oxygen concentration at the position of the worker is measured; and 5) By attaching the oxygen concentration sensor to the partition at the boundary between the working area and the non-working area, a decrease in the oxygen concentration is immediately detected, and the worker does not need to carry the oxygen concentration sensor in the working area.

LIST OF REFERENCE NUMERALS

2 Purge stocker, 4 Stocker main body, 6 Inner space, 8 Cell, 10 Article, 12 Working area, 14 Non-working area, 16 Stacker crane, 17 Rail, 18 Elevating pedestal, 19 Mast, 20 Door, 22 Stocker controller, 24 Purging controller, 26 Purge gas control board, 28 Purge gas pipe, 30 Partition, 31 Leg, 32 Hand-operated valve, 34 Regulator, 36 Control valve, 38 Mass flow controller, 40 Nozzle, 42 Communication unit, 44 Logic unit, 46 Touch panel, 48 Keyboard, 50 Working area setup unit, 52 Input/output, 54 Oxygen concentration sensor, 55 Sensor unit, 56 Display unit, 58 Communication unit, 60 Nozzle 62 Sampling tube, 64 Air pump

What is claimed is:

1. A purging device that performs purging with a purge gas on a plurality of articles that are supplied from outside to an inner space of the purging device, comprising:
    a setup unit configured to set up a working area in which a worker works such that the inner space of the purging device is divided into the working area and a non-working area;
    a purge gas control mechanism configured to control supply of the purge gas such that the purging of the articles is halted in the working area and is continued in the non-working area; and
    an oxygen concentration measuring device configured to measure an oxygen concentration in the working area,
    the purge gas control mechanism being configured to halt the purging of the articles in the non-working area if the oxygen concentration in the working area decreases to a predetermined value or less.

2. The purging device according to claim 1,
    wherein the oxygen concentration measuring device includes an oxygen concentration sensor configured to be carried by the worker, or an oxygen concentration sensor and a sampling tube connected to the oxygen concentration sensor, the sampling tube being configured to be carried by the worker.

3. The purging device according to claim 1, further comprising,
    a partition configured to separate the working area from the non-working area, and to be installed in and removed from the inner space of the purging device.

4. The purging device according to claim 3,
    wherein the oxygen concentration measuring device is attached to the partition so as to measure the oxygen concentration in the working area.

5. The purging device according to claim 1, wherein
    the purging device is a purge stocker that has a door through which the worker enters and exits the inner space,
    the inner space includes a rack in which a plurality of cells are arranged along a horizontal direction and a vertical direction, and a transport device configured to transport the articles,
    the cells of the rack respectively have nozzles via which a nitrogen gas serving as the purge gas is supplied to the inside of the articles,
    the inner space is configured to be supplied with clean air from a ceiling part, and the oxygen concentration of the inner space depends on a flow of the nitrogen gas discharged from the articles and a flow of the clean air from the ceiling part, and
    the setup unit is configured to set up the working area in terms of a column of cells along the vertical direction such that the working area continuously covers a region from the door to an area in which the worker performs a work.

6. The purging device according to claim 5,
    wherein the purge gas control mechanism includes a communication unit configured to directly communicate with the oxygen sensor.

7. The purging device according to claim 6, wherein
    a plurality of the oxygen sensors are provided,
    the communication unit is configured to directly communicate with the plurality of oxygen sensors, and
    the purge gas control mechanism includes a logic unit that is configured to detect a decrease in the oxygen concentration in the working area based on a combination of signals of the plurality of oxygen sensors from the communication unit.

8. A purging method for performing, using a purging device, purging with a purge gas on a plurality of articles that are supplied from outside to an inner space of the purging device, the method comprising:
    a step for setting up a working area in which a worker works such that the inner space of the purging device is divided into the working area and a non-working area;
    a step for causing the purging device to control supply of the purge gas such that the purging of the articles is halted in the working area and is continued in the non-working area;
    a step for measuring an oxygen concentration in the working area; and
    a step for causing the purging device to halt the purging of the articles in the non-working area by the purge gas control mechanism if the oxygen concentration in the working area decreases to a predetermined value or less.

9. The purging method according to claim 8,
    wherein the purging device is a purge stocker that has a door through which the worker enters and exits the inner space,
    wherein the inner space includes a rack in which a plurality of cells are arranged along a horizontal direction and a vertical direction, and a transport device configured to transport the articles,
    wherein the cells of the rack respectively have nozzles via which a nitrogen gas serving as the purge gas is supplied to the inside of the articles,
    wherein the inner space is configured to be supplied with clean air from a ceiling part, and the oxygen concentration of the inner space depends on a flow of the nitrogen gas discharged from the articles and a flow of the clean air from the ceiling part, and
    wherein in the setting up step, the working area is set up, in terms of a column of cells along the vertical direction, so as to continuously cover a region from the door to an area in which the worker performs a work.

* * * * *